United States Patent [19]

Cho et al.

[11] Patent Number: 5,498,730
[45] Date of Patent: Mar. 12, 1996

[54] FLUORINATED ALKYL COMPOUND DERIVATIVES AND PROCESS FOR PREPARING SAME

[75] Inventors: Kwang-Yun Cho; Bum-Tae Kim; Young-Sup Kim; Yong-Ki Min; No-Kyun Park, all of Daejeon; In-Howa Jeong, Wonju, all of Rep. of Korea

[73] Assignee: Korea Research Institute of Chemical Technology, Daejeon, Rep. of Korea

[21] Appl. No.: 280,477

[22] Filed: Jul. 26, 1994

[30] Foreign Application Priority Data

Aug. 2, 1993 [KR] Rep. of Korea .................. 93-14927

[51] Int. Cl.$^6$ .................................................. C07D 333/16
[52] U.S. Cl. ........................... 549/78; 568/56; 568/57
[58] Field of Search .................... 568/56, 57; 549/78

[56] References Cited

PUBLICATIONS

Jeong et al, Chem. Abst., vol. 115, #279,532m (1991).
Jeong et al, Chem. Abst., vol. 120, #76,967n (1994).
Jeong et al, Chem. Abst., vol. 118, #80,458y (1993).
Markovskii et al, Chem. Abst., vol. 117, #150,502 (1992).

*Primary Examiner*—James H. Reamer
*Attorney, Agent, or Firm*—Darby & Darby

[57] ABSTRACT

The present invention provides fluorinated alkyl compound derivatives represented by formula of:

$$\underset{\underset{SPh}{|}}{\overset{\overset{SPh}{|}}{R-C-R_f}} \quad (I)$$

wherein:
  R is $C_{2-4}$ lower alkyl, cyclohexyl or thiophene; phenyl substituted with hydrogen, $C_{1-6}$ alkyl, haloalkyl, halogen or alkoxy; and,
  $R_f$ is fluorinated $C_{1-3}$ lower alkyl.

The fluorinated alkyl compound derivatives of the invention can be used as agrochemicals, drugs and intermediates therefor. The present invention also provides a novel process for preparing the fluorinated alkyl compound derivatives (I).

1 Claim, No Drawings

FLUORINATED ALKYL COMPOUND DERIVATIVES AND PROCESS FOR PREPARING SAME

FIELD OF THE INVENTION

The present invention relates to novel fluorinated alkyl compound derivatives which can be used as intermediates for agrochemicals and drugs, and novel process for preparing same.

BACKGROUND OF THE INVENTION

Fluorinated alkyl compound derivatives have been used as agrochemicals, drugs and intermediates therefor; and processes for preparing various derivatives of the fluorinated alkyl compounds have been known in the art.

In general, the fluorinated alkyl compounds have been prepared by the processes entailing multiple synthetic steps (see: JP 02121961; JP 62190133; JP 8110121; DE 3801248; and, GB 1156912). The processes of the prior art, therefore, have proven to be less than satisfactory in the sense that they do not provide the compounds in a simple and economical manner, because the processes essentially employed reactants hard to handle, and very long, complex and vigorous reaction steps to provide unstable intermediates and the productivities thereofs were relatively low. Accordingly, the processes of prior art have been restricted in light of practical application; in this connection, there have been efforts to develop the fluorinated alkyl compound derivatives in a simple and economical manner.

For instance, K. Tanaka et al discloses a process for preparing fluorinated alkyl compound derivatives substituted with diethylthio group; the process, however, has proven to be less satisfactory in the sense of low yield(52%) since trifluoroacetaldehyde hydrate obtained by reduction of methyl trifluoroacetate with lithium aluminum hydride was employed as a starting material (see: K. Tanaka et al., Chemistry Letters, 175–178(1979)).

S. T. Purrington et al also discloses a process for preparing fluorinated alkyl compound derivatives substituted with diphenylthio group; the process, however, has also proven to be less satisfactory in the sense of low yield (65%) and has not provide various derivatives, since trifluoroacetaldehyde ethylhemiacetal, phosphorus pentaoxide and hexamethyldisiloxane were employed as reactants (See: S. T. Purrington, Journal of Fluorine Chemistry, 43:229–234(1989)).

Accordingly, there is a need in the art for the development of a practical process which can be employed in industrial application.

SUMMARY OF THE INVENTION

In accordance with the present invention, the inventors developed novel fluorinated alkyl compound derivatives and a simple and economical process for preparing same from fluorinated alkylketone compounds by employing two-step process.

A primary object of the present invention is, therefore, to provide fluorinated alkyl compound derivatives represented by formula of:

(I)

wherein:
R is $C_{2-4}$ lower alkyl, cyclohexyl or thiophene; phenyl substituted with hydrogen, $C_{1-6}$ alkyl, haloalkyl, halogen or alkoxy; and,
$R_f$ is fluorinated $C_{1-3}$ lower alkyl.

Another object of the present invention is to provide a novel process for preparing the fluorinated alkyl compound derivatives represented by the formula (I).

DETAILED DESCRIPTION OF THE INVENTION

Fluorinated alkylketal compound derivatives of the invention represented by the formula (I) are prepared by reacting fluorinated alkylketone compound (III) with thiophenol (PhSH) in the presence of Lewis acid. The fluorinated alkyl compound derivatives (I) can be applied in the preparation of the other fluorinated alkyl compounds represented by the formula (II) and intermediates for fluorinated alkene compounds.

Fluorinated alkyl compound derivatives of the invention can be prepared by employing the following two-step process, which should not be taken to limit the process of the invention.

Step 1:

Dithioketal compound represented by the formula (I)(R and $R_f$ are as previously defined) is prepared by reacting fluorinated alkylketone compound represented by the formula (III) with thiophenol(PhSH) in the presence of Lewis acid. As reaction solvent, halogenated hydrocarbons such as dichloromethane, dichloroethane and carbon tetrachloride which do not affect on the reaction, are used in the reaction; and, the reaction is preferably carried out for 2 to 48 hrs at the temperature range of from −78° C. to boiling point of the solvent. Lewis acids such as aluminum chloride($AlCl_3$), boron trifluoride-diethyl ether($BF_3$ $OEt_2$), ferric chloride($FeCl_3$), stannic chloride(IV) and titanium chloride(IV), are employed in the reaction as the catalysts, where the catalysts are preferably employed in an equivalent ratio to afford high yield of the desired compound.

Step 2:

Fluorinated alkyl compound derivatives represented by the formula (II) are prepared by reducing the dithioketal compound represented by the formula (I) obtained in the Step 1. In this regard, Raney nickel, lithium aluminum hydride, sodium borohydride and tributyltin hydride($Bu_3SnH$), are preferably employed as reducing agents. Organic solvents such as ether, tetrahydrofuran, benzene, toluene, and mixture thereofs which do not affect on the reaction, can be employed in the reaction; and, the reaction is preferably carried out for 1 to 20 hrs, at the temperature range of from −20° C. to boiling point of the solvent. In this regard, free radical initiator can be employed as a reaction catalyst, which depends on the reaction condition.

The Step 1 and Step 2 are summarized as followings:

Step 1:

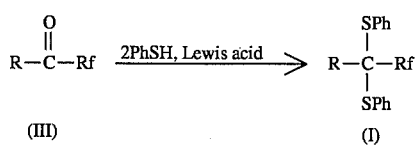

Step 2:

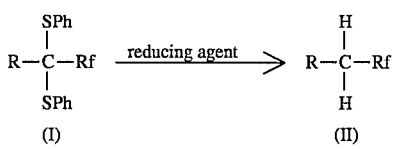

wherein:

R and $R_f$ are as previously defined.

The fluorinated alkyl compound derivatives (I) and (II) are fractionated or isolated by means of the known techniques in the art, e.g., distillation, crystallization and chromatography in accordance with their specific physicochemical character; and, identified by the spectrometric methods employing $^1$H-NMR, $^{19}$F-NMR and mass spectroscopy, etc.

The fluorinated alkyl compound derivatives (I) and (II) can be used as agrochemicals and drugs, or intermediates therefor.

The present invention is further illustrated in the following examples, which should not be taken to limit the scope of the invention

EXAMPLE 1

Preparation of 1,1-(bisphenylthio)-2,2,2-trifluoroethylbenzene

In a dried 500 ml 3-neck flask, 3.48 g(0.02 moles) of 2,2,2-trifluoroacetophenone and 4.40 g(0.04 moles) of thiophenol was added to the 200 ml of previously dried methylene chloride under the blanket of dry nitrogen, and the reaction mixture was stirred with the magnetic stirrer. The reaction mixture was cooled to −78° C. and 2.67 g(0.02 moles) of aluminum chloride was added in a dropwise. After the reaction for 20 hrs at −78° C., 100 ml of water and 150 ml of methylene chloride was added, and fractional extraction was followed to form organic layer. The organic layer thus formed was washed with water and saturated sodium chloride solution, and dried using anhydrous magnesium sulfate. The residue where the organic solvent was removed, was fractionated with column chromatography employing n-hexane as eluent to give 6.9 g of transparent crystal of 1,1-(bisphenylthio)- 2,2,2-trifluoroethylbenzene(yield: 92%). Chemical analysis was performed to identify the desired compound by the analytical methods such as $^1$H-NMR, $^{19}$F-NMR and mass spectroscopy.

m.p.: 72–73° C. $^1$H NMR(300 MHz, CDCl$_3$) δ: 7.15–7.80(m, 15H) $^{19}$F NMR(80 MHz, CDCl$_3$, CF$_3$CO$_2$H) δ: 15.80 ppm(s, 3F) MS m/e(rel. int.): 376(M+, 5), 285(100), 234(15), 197(20), 165(20), 109(13), 77(20)

EXAMPLES 2 to 21:

In an analogous manner to the process described in Example 1 except for employing the corresponding fluorinated alkylketone compounds, the reaction was carried out. The physical properties and the chemical analysis of the compounds obtained in Examples 1 to 21 were summarized in Table 1.

TABLE 1

| Example | R | $R_f$ | physical property | data of NMR and MS |
|---|---|---|---|---|
| 1 | phenyl | CF$_3$ | mp 72–73° C. | $^1$H NMR (CDCl$_3$, TMS) δ: 7.15~7.80(m, 15H)<br>$^{19}$F NMR (CDCl$_3$, CF$_3$CO$_2$H) δ: 15.80 ppm (s, 3F)<br>MS m/e (rel. int.) 376(M+, 5), 285(100), 234(15), 197(20), 165(20), 109(13), 77(20) |
| 2 | 4-F-phenyl | CF$_3$ | mp 90° C. | $^1$H NMR (CDCl$_3$, TMS) δ: 6.92~6.99(m, 2H), 7.17~7.39 (m, 10H), 7.73~7.77(m, 2H)<br>$^{19}$F NMR (CDCl$_3$, CF$_3$CO$_2$H) δ: −34.98(s, 1F), 15.69(s, 3F)<br>MS m/e (rel. int.) 394(M+, 5), 285(100), 215(13), 183(12) |
| 3 | 3-F-phenyl | CF$_3$ | mp 38° C. | $^1$H NMR (CDCl$_3$, TMS) δ: 7.0~7.71(m, 14H)<br>$^{19}$F NMR (CDCl$_3$, CF$_3$CO$_2$H) δ: 15.73(s, 3F), −34.69—34.93(m, 1F)<br>MS m/e (rel. int.) 394(M+, 5), 285(100), 215(17), 183(16) |
| 4 | 4-Cl-phenyl | CF$_3$ | oil | $^1$H NMR (CDCl$_3$, TMS) δ: 7.14~7.98(m, 14H)<br>$^{19}$F NMR (CDCl$_3$, CF$_3$CO$_2$H) δ: 15.74(s, 3F)<br>MS m/e (rel. int.) 410(M+, 1), 301(100), 233(14), 197(17) |
| 5 | 4-CF$_3$-phenyl | CF$_3$ | oil | $^1$H NMR (CDCl$_3$, TMS) δ: 7.01~8.12(m, 14H)<br>$^{19}$F NMR (CDCl$_3$, CF$_3$CO$_2$H) δ: 14.59(s, 3F), 15.94(s, 3F)<br>MS m/e (rel. int.) 444(M+, 3), 335(100), 265(15) |
| 6 | 3-CF$_3$-phenyl | CF$_3$ | oil | $^1$H NMR (CDCl$_3$, TMS) δ: 7.15~7.48(m, 11H), 7.82(d, 2H), 8.06(s, 1H)<br>$^{19}$F NMR (CDCl$_3$, CF$_3$CO$_2$H) δ: 14.49(s, 3F), 15.65(s, 3F)<br>MS m/e (rel. int.) 444(M+, 2), 335(100), 265(15) |

TABLE 1-continued

| Example | R | $R_f$ | physical property | data of NMR and MS |
|---|---|---|---|---|
| 7 | 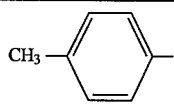 CH₃— (p-tolyl) | $CF_3$ | oil | $^1$H NMR (CDCl₃, TMS) δ: 2.29(s, 3H), 7.08(dd, 1H), 7.16~7.40(m, 11H), 7.66(d, 2H) <br> $^{19}$F NMR (CDCl₃, CF₃CO₂H) δ: 15.60(s, 3F) <br> MS m/e (rel. int.) 390(M⁺, 3), 281(100) |
| 8 | 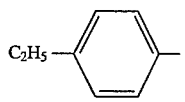 C₂H₅— (p-ethylphenyl) | $CF_3$ | oil | $^1$H NMR (CDCl₃, TMS) δ: 1.19(t, 3H), 2.60(q, 2H), 7.06~7.68(m, 14H) <br> $^{19}$F NMR (CDCl₃, CF₃CO₂H) δ: 15.61(s, 3F) <br> MS m/e (rel. int.) 404(M⁺, 2), 295(100) |
| 9 | 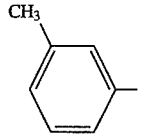 CH₃ (m-tolyl) | $CF_3$ | oil | $^1$H NMR (CDCl₃, TMS) δ: 2.28(s, 3H), 7.10~7.85(m, 14H) <br> $^{19}$F NMR (CDCl₃, CF₃CO₂H) δ: 15.62(s, 3F) <br> MS m/e (rel. int.) 390(M⁺, 3), 281(100) |
| 10 | 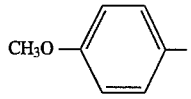 CH₃O— (p-methoxyphenyl) | $CF_3$ | oil | $^1$H NMR (CDCl₃, TMS) δ: 3.87(s, 3H), 6.77(d, 2H), 7.15~7.45(m, 10H), 7.67(d, 2H) <br> $^{19}$F NMR (CDCl₃, CF₃CO₂H) δ: 15.51(s, 3F) |
| 11 | 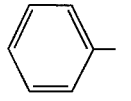 phenyl | $CF_2CF_3$ | mp 45° C. | $^1$H NMR (CDCl₃, TMS) δ: 7.10~7.85(m, 15H) <br> $^{19}$F NMR (CDCl₃, CF₃CO₂H) δ: −25.00(s, 2F), 3.57(s, 3F) <br> MS m/e (rel. int.) 426(M⁺, 2), 317(100), 71(17), 58(41) |
| 12 | 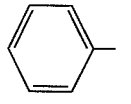 phenyl | $CF_2CF_2CF_3$ | mp 34° C. | $^1$H NMR (CDCl₃, TMS) δ: 7.31~7.39(m, 9H), 7.62~7.67(m, 6H) <br> $^{19}$F NMR (CDCl₃, CF₃CO₂H) δ: −16.94(q, 2F), −14.43(s, 2F), −32.34(t, 3F) <br> MS m/e (rel. int.) 476(M⁺, 1), 367(100), 121(23) |
| 13 | 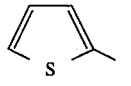 thienyl | $CF_3$ | mp 66–67° C. | $^1$H NMR (CDCl₃, TMS) δ: 6.66~6.90(m, 2H), 7.15~7.65(m, 11H) <br> MS m/e (rel. int.) 382(M⁺, 1), 273(100), 239(20), 204(15), 171(34), 127(25), 109(43), 77(52), 65(44) |
| 14 | CH₃ | $CF_3$ | oil | $^1$H NMR (CDCl₃, TMS) δ: 1.37(s, 3H), 7.24~7.43(m, 6H), 7.63~7.66(m, 4H) <br> $^{19}$F NMR (CDCl₃, CF₃CO₂H) δ: 6.26(s, 3F) <br> MS m/e (rel. int.) 314(M⁺, 12), 205(100), 165(15) |
| 15 | n-C₄H₉ | $CF_3$ | oil | $^1$H NMR (CDCl₃, TMS) δ: 0.87(t, 3H), 1.01~1.20(m, 4H), 1.62~1.88(m, 2H), 7.21~7.60(m, 10H) <br> $^{19}$F NMR (CDCl₃, CF₃CO₂H) δ: 4.47(s, 3F) |
| 16 | n-C₄H₉ | $CF_2CF_3$ | oil | $^1$H NMR (CDCl₃, TMS) δ: 0.83(t, 3H), 1.07~1.17(m, 2H), 1.66~1.77(m, 4H), 7.25~7.45(m, 6H), 7.61~7.66(m, 4H) <br> $^{19}$F NMR (CDCl₃, CF₃CO₂H) δ: −26.98(s, 2F), 2.50(s, 3F) <br> MS m/e (rel. int.) 406(M⁺, 8), 297(88), 241(22), 141(27), 109(100), 65(33) |
| 17 | CH₃CH₂ | $CF_2CF_3$ | oil | $^1$H NMR (CDCl₃, TMS) δ: 1.25(m, 3H), 1.76(q, 2H), 7.25~7.41(m, 6H), 7.60~7.64(m, 4H) <br> MS m/e (rel. int.) 378(M⁺, 3), 269(100), 218(5), 109(55), 65(9) |
| 18 | CH₃CH₂ | $n-C_3F_7$ | oil | $^1$H NMR (CDCl₃, TMS) δ: 1.25(m, 3H), 1.76(q, 2H), 7.25~7.41(m, 6H), 7.60~7.65(m, 4H) <br> MS m/e (rel. int.) 428(M⁺, 3), 319(100), 279(5), 109(60), 65(15) |
| 19 | n-C₃H₇ | $n-C_3F_7$ | oil | $^1$H NMR (CDCl₃, TMS) δ: 0.85(t, 3H), 1.78(m, 4H), 7.25~7.42(m, 6H), 7.60~7.65(m, 4H) <br> MS m/e (rel. int.) 442(M⁺, 2), 333(100), 291(36), 255(9), 109(43), 65(6) |
| 20 | 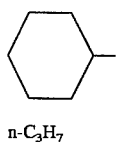 cyclohexyl | $CF_3$ | mp 91–94° C. | $^1$H NMR (CDCl₃, TMS) δ: 1.17(m, 3H), 1.52~1.69(m, 3H), 1.77~1.87,(m, 3H), 2.30(d, 2H), 7.23~7.43(m, 6H), 7.62~7.64(m, 4H) <br> MS m/e (rel. int.) 382(M⁺, 5), 273(100), 191(18), 163(27), 109(16) |
| 21 | n-C₃H₇ | $CF_3$ | oil | $^1$H NMR (CDCl₃, TMS) δ: 0.76(t, 3H), 1.65(t, 2H), 1.77~1.85(m, 2H), 7.31~7.43(m, 6H), 7.62~7.64(m, 4H) <br> MS m/e (rel. int.) 342(M⁺, 10), 233(100), 191(39), 155(12), 109(31) |

EXAMPLE 22

Preparation of 2,2,2-trifluoroethylbenzene

In a dried 500 ml flask, 4.70 g(0.0125 moles) of 1,1-(bisphenylthio)- 2,2,2-trifluoroethylbenzene prepared in Example 1, 7.62 ml(0.0275 moles) of tributyltin hydride and 0.08 g of azoisobutyronitrile(AIBN) was added and heated to 90° C. using oil bath, and the reaction mixture was stirred for 1 hr. The reaction mixture was cooled to room temperature, and was distilled under reduced pressure. The oily mixture thus obtained was subject to simple distillation to give 1.6 g of transparent liquid of 2,2,2-trifluoroethylbenzene(yield: 80%).

b.p.: 120° C. $^1$H NMR(CDCl$_3$, TMS) δ: 3.31(q, 2H), 7.2–7.4(m, 5H) $^{19}$F NMR(CDCl$_3$, CF$_3$CO$_2$H) δ: 26.23 ppm(t, 3F) MS m/e(rel. int.): 160(M+, 88), 91(100)

EXAMPLES 23 to 42

In an analogous manner to the process described in Example 22 except for employing the corresponding fluorinated dithioketal compounds obtained in Examples 1 to 21, the reaction was carried out. The physical properties and the chemical analysis of the compounds obtained in Examples 22 to 42 were summarized in Table 2.

TABLE 2

| Example | R | R$_f$ | physical property | data of NMR and MS |
|---|---|---|---|---|
| 22 | phenyl | CF$_3$ | bp 120° C. | $^1$H NMR (CDCl$_3$, TMS) δ: 3.31(q, 2H), 7.2~7.4(m, 5H)<br>$^{19}$F NMR (CDCl$_3$, CF$_3$CO$_2$H) δ: 26.23(t, 3F)<br>MS m/e (rel. int.) 160(M+, 88), 91(100) |
| 23 | 4-F-phenyl | CF$_3$ | bp 132° C.–134° C. | $^1$H NMR (CDCl$_3$, TMS) δ: 3.35(q, 2H), 7.02~7.31(m, 4H)<br>$^{19}$F NMR (CDCl$_3$, CF$_3$CO$_2$H) δ: 24.93(t, 3F), −86.46(m, 1F)<br>MS m/e (rel. int.) 178(M+, 100), 109(76) |
| 24 | 3-F-phenyl | CF$_3$ | bp 136° C.–138° C. | $^1$H NMR (CDCl$_3$, TMS) δ: 3.35(q, 2H), 6.95~7.40(m, 4H)<br>$^{19}$F NMR (CDCl$_3$, CF$_3$CO$_2$H) δ: 26.42(t, 3F), −82.59(m, 1F)<br>MS m/e (rel. int.) 178(M+, 100), 109(52) |
| 25 | 4-Cl-phenyl | CF$_3$ | bp 168° C.–170° C. | $^1$H NMR (CDCl$_3$, TMS) δ: 3.34(q, 2H), 7.46(q, 4H) |
| 26 | 4-CF$_3$-phenyl | CF$_3$ | bp 151° C.–152° C. | $^1$H NMR (CDCl$_3$, TMS) δ: 3.43(q, 2H), 7.48(q, 4H)<br>$^{19}$F NMR (CDCl$_3$, CF$_3$CO$_2$H) δ: 26.21(t, 3F), 33.23(s, 3F)<br>MS m/e (rel. int.) 228(M+, 100), 174(15), 159(79) |
| 27 | 3-F$_3$C-phenyl | CF$_3$ | bp 146° C.–147° C. | $^1$H NMR (CDCl$_3$, TMS) δ: 3.43(q, 2H), 7.25~7.64(m, 4H)<br>$^{19}$F NMR (CDCl$_3$, CF$_3$CO$_2$H) δ: 25.54(t, 3F), 32.91(s, 3F)<br>MS m/e (rel. int.) 228(M+,100), 178(250), 159(70) |
| 28 | 4-CH$_3$-phenyl | CF$_3$ | mp 44–45° C. | $^1$H NMR (CDCl$_3$, TMS) δ: 2.31(s, 3H), 3.26(q, 2H), 7.14(s, 4H)<br>$^{19}$F NMR (CDCl$_3$, CF$_3$CO$_2$H) δ: 25.92(t, 3F)<br>MS m/e (rel. int.) 174(M+, 100), 105(86) |
| 29 | 3-CH$_3$-phenyl | CF$_3$ | bp 158° C. | $^1$H NMR (CDCl$_3$, TMS) δ: 2.34(s, 3H), 3.29(q, 2H), 7.05–7.28(m, 4H)<br>$^{19}$F NMR (CDCl$_3$, CF$_3$CO$_2$H) δ: 26.60(t, 3F)<br>MS m/e (rel. int.) 174(M+, 73), 105(100) |
| 30 | 4-CH$_3$O-phenyl | CF$_3$ | bp 158° C. | $^1$H NMR (CDCl$_3$, TMS) δ: 3.28(q, 2H), 3.79(s, 3H), 7.08(q, 4H)<br>$^{19}$F NMR (CDCl$_3$, CF$_3$CO$_2$H) δ: 25.12(t, 3F)<br>MS m/e (rel. int.) 190(M+, 96), 121(100) |
| 31 | phenyl | CF$_2$CF$_3$ | bp 130–134° C. | $^1$H NMR (CDCl$_3$, TMS) δ: 3.31(t, 2H), 7.23~7.39(m, 5H)<br>$^{19}$F NMR (CDCl$_3$, CF$_3$CO$_2$H) δ: −17.95(s, 3F) −92.37(t, 2F)<br>MS m/e (rel. int.) 210(M+, 100), 91(94) |

TABLE 2-continued

| Example | R | $R_f$ | physical property | data of NMR and MS |
|---|---|---|---|---|
| 32 | 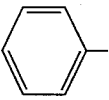 | n-$C_3F_7$ | bp 138–140° C. | $^1$H NMR (CDCl$_3$, TMS) δ: 3.32(dt, 2H), 7.21~7.40(m, 5H)<br>$^{19}$F NMR (CDCl$_3$, CF$_3$CO$_2$H) δ: −8.21(t, 3F), −85.58(t, 2F), −116.62 (s, 2F)<br>MS m/e (rel. int.) 260(M$^+$, 100), 228(11), 159(10), 91(89) |
| 33 | 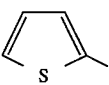 | CF$_3$ | bp 122–124° C. | $^1$H NMR (CDCl$_3$, TMS) δ: 3.52 (q, 2H), 6.95~7.25(m, 3H)<br>$^{19}$F NMR (CDCl$_3$, CF$_3$CO$_2$H) δ: 24.20(t, 3F)<br>MS m/e (rel. int.) 166(M$^+$, 100), 97(99) |
| 34 | CH$_3$ | CF$_3$ | bp −12–13° C. | $^1$H NMR (CDCl$_3$, TMS) δ: 1.10(t, 3H), 2.01~2.18(m, 2H) |
| 35 | n-C$_3$H$_7$ | CF$_3$ | bp 28–30° C. | $^1$H NMR (CDCl$_3$, δ: 0.94(t, 3H), 1.32~1.46(m, 2H), 1.49~1.59(m, 2H), 2.01~2.11(m, 2H)<br>MS m/e (rel. int.) 126(M$^+$, 4), 106(10), 91(9), 78(22), 47 (23), 42(100) |
| 36 | CH$_3$CH$_2$ | CF$_2$CF$_3$ | bp 46–48° C. | $^1$H NMR (CDCl$_3$, TMS) δ: 1.06(t, 3H), 1.54~1.69(m, 2H), 2.01~2.18(m, 2H)<br>MS m/e (rel. int.) 162(M$^+$, 2), 119(5), 93(100), 77(22), 73 (35), 69(12), 65(21) |
| 37 | n-C$_4$H$_9$ | CF$_2$CF$_3$ | bp 90–92° C. | $^1$H NMR (CDCl$_3$, TMS) δ: 0.93(t, 3H), 1.54~1.69(m, 6H), 1.90~2.08(m, 2H)<br>MS m/e (rel. int.) 190(M$^+$, 4), 175(12), 160(10), 141(9), 121(15), 91(42), 77(39), 69(35), 64(20), 55(20), 43(100) |
| 38 | CH$_3$CH$_2$ | n-C$_3$F$_7$ | bp 64–65° C. | $^1$H NMR (CDCl$_3$, TMS) δ: 1.03(t, 3H), 1.55~1.72(m, 2H), 1.93~2.12(m, 2H)<br>MS m/e (rel. int.) 212(M$^+$, 2), 191(4), 173(9), 145(12), 127(23), 119(18), 100(18), 93(100), 77(35), 73(99), 69 (50), 65(73), 47(37), 43(30) |
| 39 | n-C$_3$H$_7$ | n-C$_3$F$_7$ | bp 88–90° C. | $^1$H NMR (CDCl$_3$, TMS) δ: 0.95(t, 3H), 1.31~1.47(m, 2H), 1.53~1.64(m, 2H), 1.95~2.13(m, 2H)<br>MS m/e (rel. int.) 226(M$^+$, 23), 205(10), 191(10), 177 (17), 145(30), 127(18), 107(100), 100(10), 87(85), 77 (54), 69(36), 55(85), 47(53) |
| 40 | 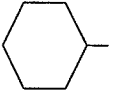 | CF$_3$ | bp 128–130° C. | $^1$H NMR (CDCl$_3$, TMS) δ: 0.86~1.32(m, 5H), 1.62~1.83 (m, 6H), 1.97(dq, 2H)<br>MS m/e (rel. int.) 166(M$^+$, 12), 123(2), 83(100), 69 (7), 55(34), 41(15) |
| 41 | 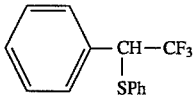 | | oil | $^1$H NMR (CDCl$_3$, TMS) δ: 4.50(q, 1H), 7.20~7.44(m, 10H)<br>MS m/e (rel. int.) 268(M$^+$, 100), 199(12), 159(52) |
| 42 | 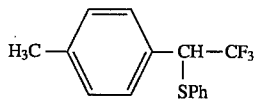 | | oil | $^1$H NMR (CDCl$_3$, TMS) δ: 2.33(s, 3H), 4.66(q, 1H), 7.11~7.44(m, 9H)<br>MS m/e (rel. int.) 282(M$^+$, 26), 173(100), 123(57) |

As well be seen in the aboves, the present invention provides novel fluorinated alkyl compound derivatives which can be used as agrochemicals, drugs and intermediates therefor, and novel process for preparing same.

What is claimed is:

1. A Fluorinated alkyl compound derivative represented by the formula:

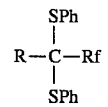

wherein:
R is cyclohexyl, thiophene or phenyl substituted with alkoxy; and,
$R_f$ is fluorinated $C_{1-3}$ lower alkyl.

* * * * *